United States Patent [19]
Adachi et al.

[11] Patent Number: 5,794,337
[45] Date of Patent: Aug. 18, 1998

[54] VALVE SEAT AND TEST PROCEDURE

[75] Inventors: Shuhei Adachi; Junichi Inami, both of Iwata, Japan

[73] Assignee: Yamaha Hatsudoki Kabushiki Kaisha, Iwata, Japan

[21] Appl. No.: 638,980

[22] Filed: Apr. 25, 1996

[30] Foreign Application Priority Data

Apr. 26, 1995 [JP] Japan .................................. 7-102016

[51] Int. Cl.$^6$ ...................................................... B23P 11/00
[52] U.S. Cl. ...................... 29/888.44; 29/888.061
[58] Field of Search ......................... 29/888.44, 888.061; 123/188.8

[56] References Cited

U.S. PATENT DOCUMENTS 5,492,091  2/1996  Russ ..................................... 29/888.061
5,653,377  8/1997  Reatherford et al. .................. 29/888.44

FOREIGN PATENT DOCUMENTS 0224345  6/1987  European Pat. Off. .
0259023  3/1988  European Pat. Off. .
873203   7/1942  France .
1352656  5/1964  France .
698709  11/1940  Germany .
658116   3/1994  Japan ................................... 29/888.44

OTHER PUBLICATIONS

Patent Abstracts of Japan, vol. 006, No. 059 (P–110), 16 Apr. 1982.
Databse WPI, Section EI, Week 9018, 13 Jun. 1990.
European Search Report dated Aug. 7, 1996.

*Primary Examiner*—Erick R. Solis
*Attorney, Agent, or Firm*—Knobbe, Martens, Olson & Bear LLP

[57] ABSTRACT

A method of forming a bonded valve seat and testing the resulting bond strength in ensure that the desired characteristics have been achieved. The testing is done both during the bonding process and at the completion of the process.

29 Claims, 10 Drawing Sheets

VALVE SEAT AND TEST PROCEDURE

BACKGROUND OF THE INVENTION

This invention relates to a valve seat arrangement for a reciprocating machine and more particularly to an improved test procedure for a bonded valve seat for an internal combustion engine.

In internal combustion engines, it frequently is the practice to employ aluminum or aluminum alloys as the material for a number of the major engine castings such as the cylinder heads. When the cylinder heads are formed from aluminum or aluminum alloys, however, certain components of the cylinder head are formed from a dissimilar material so as to improve performance. For example, the valve seats of the cylinder head are normally formed from a harder, less heat conductive material such as iron or ferrous iron alloys. By utilizing such harder materials, the valve seat life can be extended. However, the attachment of the dissimilar valve seat insert into the cylinder head presents a number of problems.

Conventionally, it has been the practice to form the cylinder head passages with recesses adjacent the seating area into which the insert rings which form the valve seat are press fit. The use of press fitting has a number of disadvantages. These disadvantages may be understood by reference to FIG. 1 which shows a conventional pressed in type of valve seat.

The cylinder head material 21 is formed with a counterbore 22 at the cylinder head recess side of the flow passage 23. The flow passage 23 may be either an intake passage or an exhaust passage. The insert ring is indicated by the reference numeral 24 and may be formed from any suitable material, such as a Sintered ferrous material. Such materials have the advantage of having high wear capabilities. After the insert 24 has been pressed into place, its surface is machined as at 25 so as to form the actual valve seating surface.

As may be seen, this technique requires relatively large valve seat inserts in order to withstand the pressing pressures. In addition, the press fit must be such that the insert ring will not fall out when the engine is running. As a result, there are quite high stresses exerted both on the cylinder head and on the insert ring. The stresses can result in loads which may eventually cause cracks in the cylinder head.

These types of construction also limit the maximum size and spacing of the valve seats in order to ensure adequate cylinder head material between adjacent valve seats to reduce the likelihood of cracking. In addition, the large seats compromise the configuration of the intake passages, particularly at the critical valve seating area. Finally, these constructions result in somewhat poor heat transfer from the valve to the cylinder head due to the poor thermal conductivity of the valve seat material and the poor contact area between the insert 24 and the cylinder head 21.

In addition, the interface between the insert ring and the cylinder head frequently leaves voids or air gaps which further reduce the heat transfer and thus cause the valves to run at a higher temperature. This higher temperature operation of the valves requires the valves to be made heavier and stronger and thus reduce the performance of the engine and increase its size and costs.

Many of these problems become worse as the engine reaches operating or higher temperatures. Because of the higher coefficient of expansion of the cylinder head material, the press fit force diminishes and the contact area for heat transfer also decreases.

It has been proposed, therefore, to utilize a technology wherein the insert ring is laser clad into the cylinder head. Such a cylinder head assembly is shown in FIG. 2.

In this technique, a somewhat smaller insert ring 26 is laser clad into the cylinder head material 21. This results in a bonding interface 27 that is formed between melt reaction layers 28 and 29 of the cylinder head material 21 and insert ring material 26. These actually form alloys.

Such laser cladding generally ensures against the likelihood of stresses which may cause cracking. Nevertheless, the laser cladding technique itself requires rather large inserts and thus a number of the disadvantages with pressed in inserts also are found with welded inserts. Furthermore, the heat transfer problems are also prevalent and in some instances can become worsened.

With a laser cladding technique, there is actually formed a metallurgical alloy between the material of the insert ring and the cylinder head. Because of the fusion process, air pockets or voids may occur in the areas 28 and 29 and heat transfer is reduced. In addition, the alloy at the interface between the insert ring and the cylinder head also has poor thermal conductivity and thus a number of the problems present with pressed in inserts are also present with laser clad inserts.

Another difficulty with the types of valve seat formation shown in FIGS. 1 and 2 is that the resulting valve seat does not afford any structure that will facilitate the testing of the bonding strength between the insert and the cylinder head. In order to provide a way in which the joint can be tested, it is necessary to either machine the insert so as to accept a pulling tool, or in the case of a pressed in insert, to have the insert have a projecting ledge that will afford access to a pulling tool. However, by increasing the size of the insert to achieve this testing, then the insert itself does not correspond to the final finished insert and the testing will not be reliable.

It is, therefore, a principal object of this invention to provide an improved method for testing a valve seat formed through the use of an insert formed from a different material than that of the cylinder head.

It has been proposed to employ a technique wherein the insert ring is metallurgically bonded but not alloyed to the cylinder head material. This is accomplished by pressing the insert into place and passing an electrical current through the insert which is sufficient to cause the cylinder head material to plastically deform upon insertion of the insert ring. The plastically deformed phase of the cylinder head material forms a metallurgical bond at the interface with the insert ring without any significant resulting alloying of the cylinder head material to that of the insert ring. Such an arrangement is disclosed in our co-pending application entitled, "Valve Seat Bonded Cylinder Head and Method for Producing Same," application Ser. No. 08/483,246, filed Jun. 7, 1995 and assigned to the assignee hereof. In addition, certain of these techniques are also described in our co-pending application entitled "VALVE SEAT," application Ser. No. 08/278,026, filed Jul. 20, 1994, in the names of Shuhei Adachi & Junichi Inami and also assigned to the Assignee hereof.

These techniques have a number of advantages over the conventional structures. First, they permit the use of much smaller insert rings since the pressing pressure is reduced and thus the shape of the intake passage, particularly the shape of the cylinder head passages, particularly in the critical area of the valve seats are not compromised. In addition, the bond strength is considerably higher than more conventional methods. Furthermore, this technique, because of the improved way in which the adhesion is formed, permits the use of much smaller insert rings and thus permits the valve seat openings to be positioned closer to each other without the likelihood of causing defects in the cylinder head which may manifest themselves during the engine running and life.

Anther advantage of this type of bonding technique or technique for forming inserts is that it lends itself to a very easy way in which the strength of the bond can be tested. This is partially a result of the fact that the insert ring can be easily formed with a projecting shoulder which will permit testing without the test being not truly indicative of the strength of the bond.

It is, therefore, a still further object of this invention to provide an improved test procedure for testing the strength of a bonded valve seat insert joint.

In addition to the pulling test for testing the strength of the joint, it is a still further object of this invention to provide a number of other test procedures that can be employed so as to test the validity and strength of the resulting metallurgically bonded joint.

SUMMARY OF THE INVENTION

A first feature of this invention is adapted to be embodied in a method of affixing and testing a valve seat insert in a cylinder head having a flow passage ending in a combustion chamber recess. The method comprises the steps of forming a recess in the cylinder head at the base of the flow passage and forming an insert to be received in the recess. The insert has an opening adapted to form a flow opening registering with the cylinder head flow passage and an outer surface positioned to engage the part of the cylinder head defining the recess. The insert is placed in alignment with the recess and pressure is applied to the cylinder head and the insert for forcing the insert into the recess. An electrical current is passed through the pressing member, the insert and the cylinder head during at least a portion of the pressing operation to heat the cylinder head and metallurgically bond the insert and the cylinder head. The amount of depression of the insert into the recess in respect to time is measured and compared with a known range of values to assure that the bonding of the insert to the cylinder head is satisfactory.

Another feature of the invention is adapted to be embodied in a method of affixing and testing a valve seat insert in a cylinder head having a flow passage ending in a combustion chamber recess. The method comprises the steps of forming a recess in the cylinder head at the base of the flow passage and forming an insert to be received in the recess and having an opening adapted to form a flow opening registering with the cylinder head flow passage and an outer surface positioned to engage the part of the cylinder head defining the recess. The insert is placed in alignment with the recess. Pressure is applied to the cylinder head and the insert for forcing the insert into the recess. An electrical current is passed through the pressing member, the insert and the cylinder head during at least a portion of the pressing operation to heat the cylinder head and metallurgically bond the insert and the cylinder head. The insert is sized to form an inwardly projecting shoulder around the recess at the end of the bonding step. A pulling force is applied to the shoulder while restraining the cylinder head to measure the force required to separate the bonded insert from the cylinder head.

A further feature of the invention is adapted to be embodied in a method of affixing and testing a valve seat insert in a cylinder head having a flow passage ending in a combustion chamber recess. The method comprises the steps of forming a recess in the cylinder head at the base of the flow passage and forming an insert to be received in the recess and having an opening adapted to form a flow opening registering with the cylinder head flow passage and an outer surface positioned to engage the part of the cylinder head defining the recess. A coating is placed on at least the portion of the insert that will contact the portion of the cylinder head that forms the recess. The insert is placed in alignment with the recess. Pressure is applied to the cylinder head and the insert for forcing the insert into the recess. An electrical current is passed through the pressing member, the insert and the cylinder head during at least a portion of the pressing operation to heat the cylinder head. The amount of electrical current flow through the insert and the cylinder head is sufficient to melt the coating and form an eutectic alloy with the cylinder head material. The pressure is applied until the eutectic alloy is substantially extruded from the area between the insert and the cylinder head and metallurgically bond the insert and cylinder head. The resulting bond is then inspected to insure that eutectic alloy has been extruded around the entire resulting joint.

DETAILED DESCRIPTION OF THE PREFERRED EMBODIMENTS OF THE INVENTION

It should be noted that the actual mechanical way in which the bond is formed with the valve seat is as described in the aforenoted co-pending applications, the disclosures of which are incorporated herein by reference. Even though these disclosures are incorporated herein by reference and the invention in this application deals primarily with the pressing method, a general description of the bonding process will also be included. However, where further information is required, reference may be had to the aforenoted co-pending applications.

Figure 1:
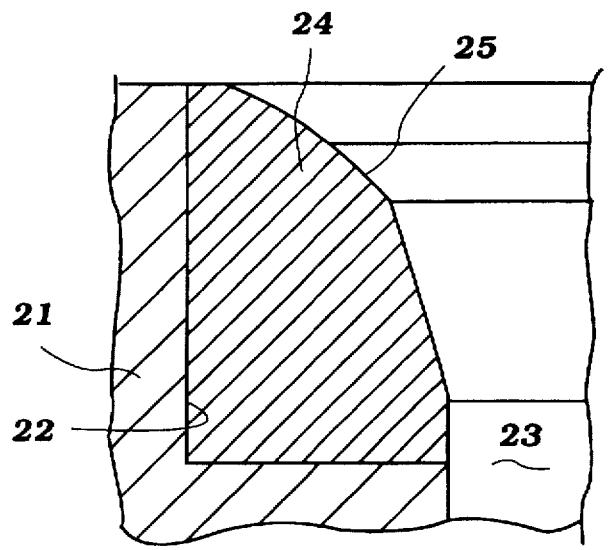
FIG. 1 is an enlarged cross-sectional view taken through a conventional prior art-type pressed in valve seat.
Figure 2:
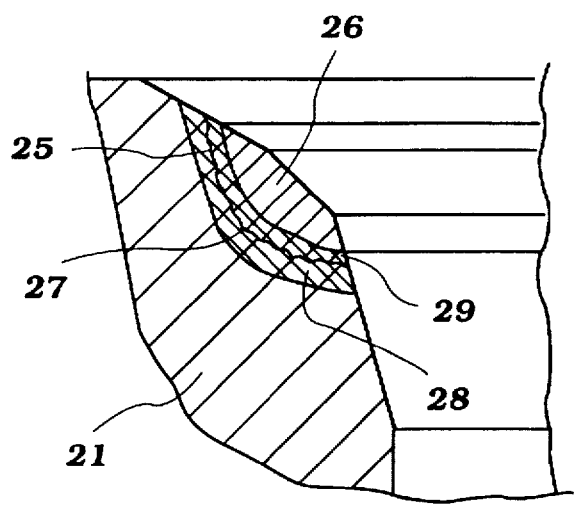
FIG. 2 is an enlarged cross-section view, in part similar to FIG. 1, and shows a conventional laser clad type valve seat.
Figure 3:
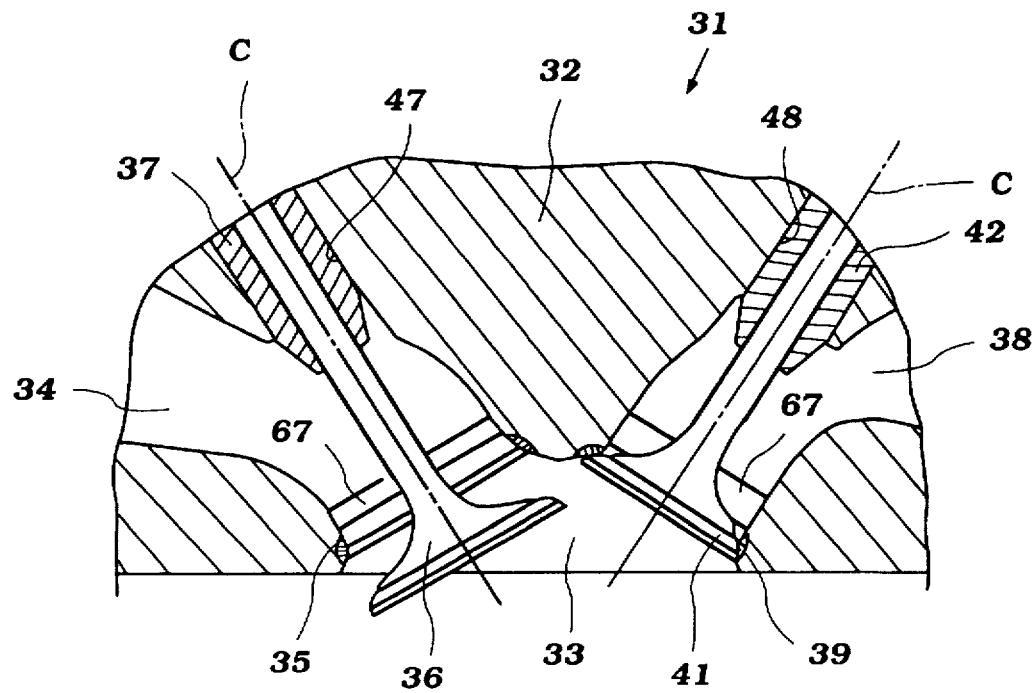
FIG. 3 is a partial cross-sectional view taken through a cylinder head having valve seats formed and constructed in accordance with the invention.

Referring first to FIG. 3, a cylinder head for an internal combustion engine utilizing the invention is identified generally by the reference numeral 31. The cylinder head includes a base cylinder head casting 32 which is formed from an aluminum or aluminum alloy. Such materials are highly desirable for use in engine components and particularly cylinder heads because of their light weight and high thermal conductivity and specific, preferred materials will be disclosed later herein.

The cylinder head 32 is formed with combustion chamber recesses 33 which cooperate with the associated cylinder bore and piston (both of which are not shown) of the associated engine to form its combustion chambers. An intake charge is delivered to these combustion chambers through one or more intake passages 34 that are formed in the cylinder head material 32 and which terminate at valve seat 35 within the cylinder head recess 33. Poppet type intake valves 36 are supported within the cylinder head 32 by valve guides 37 for controlling the opening and closing of the valve seats 35 in a well known manner. The intake valves 36 may be operated by any known type of valve actuating mechanism.

One or more exhaust passages 38 extend from the cylinder head recesses 33 and specifically from valve seats 39 formed therein for the discharge of the combustion products from the combustion recesses 33 in a manner also well known in this art. Exhaust valves 41 are slidably supported in the cylinder head 32 by valve guides 42. These exhaust valves 41, like the intake valves 36 are operated by any known type of mechanism.

Figure 4:
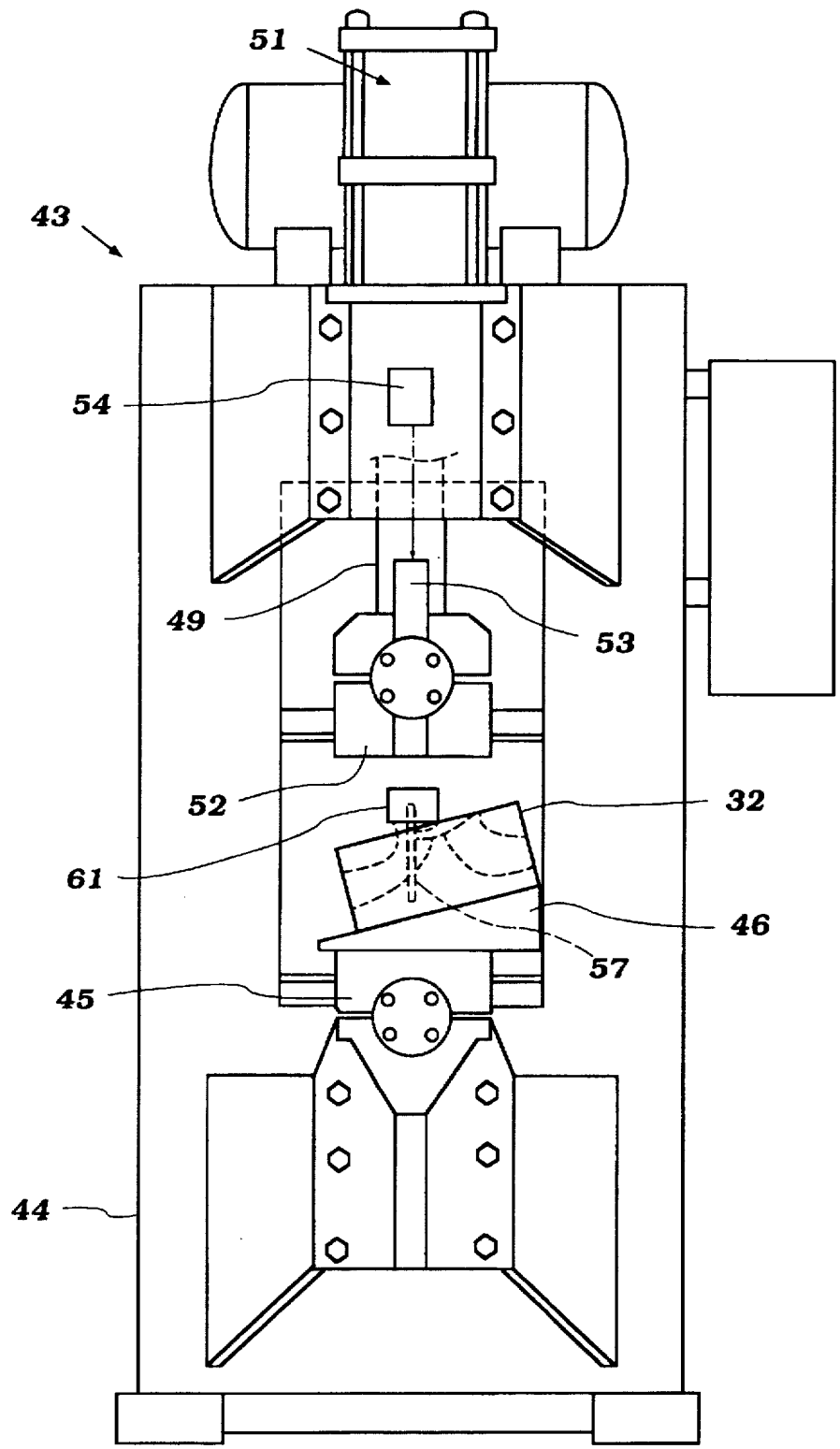
FIG. 4 is a front elevational view of an apparatus for practicing the invention for making bonded valve seats.
Figure 5:
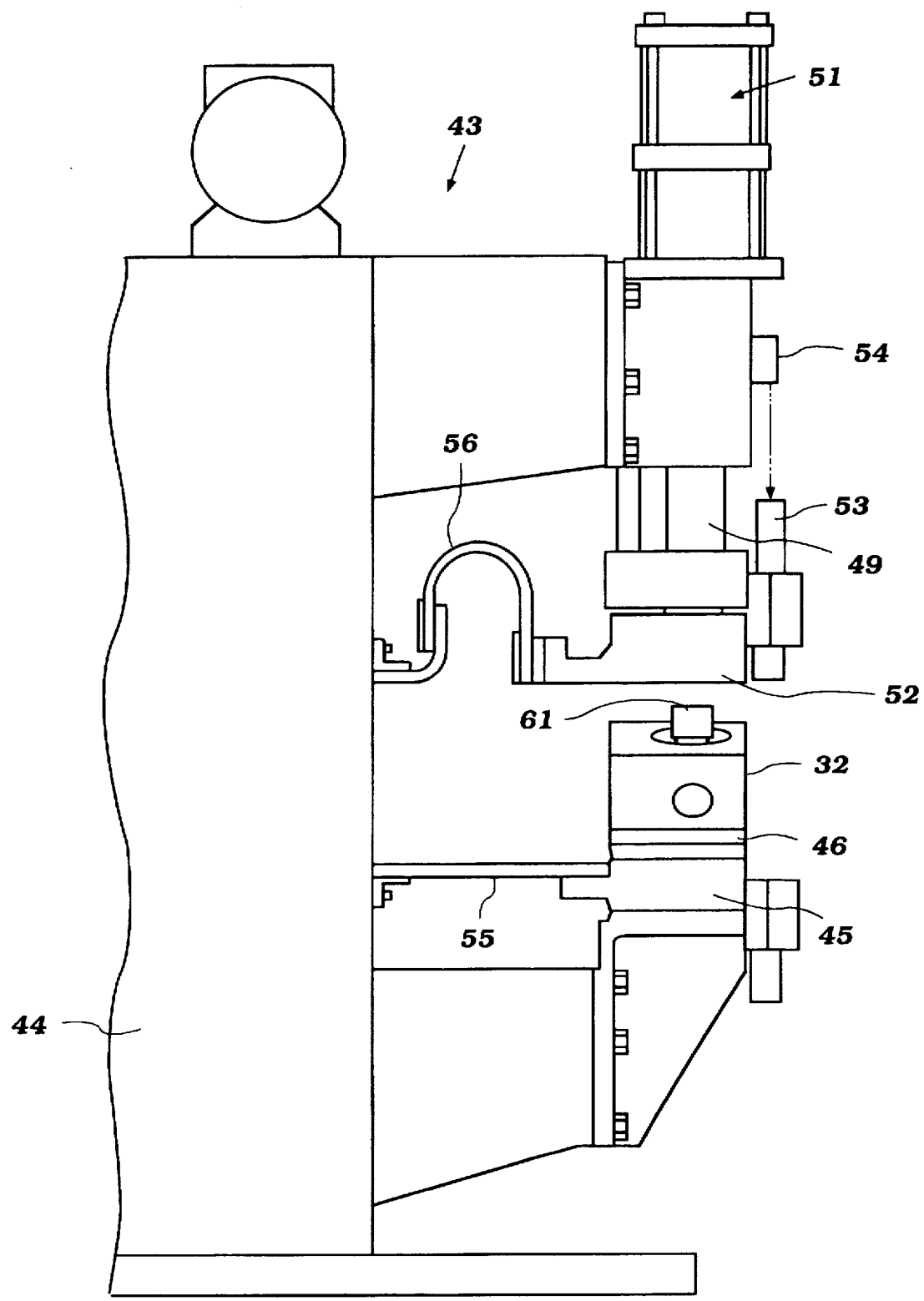
FIG. 5 is a side elevational view of the apparatus.

The invention, as should be readily apparent from the foregoing description, deals in the method in which the valve seats 35 and 39 are formed and the methods for inspecting and testing the resulting joint. This apparatus for forming the bonded joint is shown best in FIGS. 4–6 and will be discussed and described by reference to these figures.

The apparatus is indicated generally by the reference numeral 43 and may be considered to be similar to a pressure welding apparatus. However, and as will become apparent, the actual electrical current flow is not sufficient to cause any welding of the insert rings to the cylinder head material.

The apparatus 43 is comprised of a press base 44 that has a support element 45 on which a fixture 46 is mounted so as to accommodate a cylinder head 32. The fixture 46 is disposed so that the cylinder head 32 will be held at an angle. This angle is such that one of bores 47 or 48 (FIG. 3) that received the valve guides 37 or 42 will be in line with the pressing axis of the equipment.

Supported above the table or base 45 is a ram 49 which is driven by a hydraulic or pneumatic motor 51. The ram 49 carries a pressing electrode member, indicated generally by the reference numeral 52.

Affixed to the pressing electrode member 52 is an adjustable post 53 which cooperates with a proximity sensor or detector 54 such as a laser which is utilized to determine the degree of movement during the pressing of the inserts in place and the degree of movement of the ram 49 specifically. The output of this detector 54 indicates the depth at which the insert is pressed into the cylinder head, as will become apparent.

The base 44 carries a source of high energy electricity that is transmitted to the base plate 45 through a first conductor 55 and to the pressing member 52 through a second conductor 56. The conductors 55 and 56 will accommodate vertical movement and the conductor 56 is so configured in this embodiment. The pressing electrode 52 is preferably charged positively and the support base 45 is negatively charged.

The actual pressing apparatus and its association with the cylinder head will now be described by reference FIG. 6. As seen in this figure, a mandrel post, indicated generally by the reference numeral 57, is placed into the valve guide opening 47 of the cylinder head 32. The mandrel post 57 is formed from a central post part 58 that is formed from a suitable material, such as a metallic rod. However, in order to provide electrical insulation, for a reason which will become apparent, the rod 58 is provided with an insulating coating 59. Although the insulating coating 59 may be of any material, a ceramic material, such as alumina, is preferred. The alumina coating 59 is flame sprayed onto the rod base 58 and then is finished by polishing.

A stopper ring 60 is affixed to the mandrel 57 and contacts the inner surface of the cylinder head intake passage 34 around the valve guide opening 47 so as to limit how far the mandrel post 57 extends into the valve guide opening 47.

A further pressing member, indicated generally by the reference numeral 61, is provided with an opening 62 complementary in shape to the mandrel and is slid thereover. The pressing member 61 has an actual pressing surface that is formed by a hardened body 63 formed from an appropriate material and which either is magnetized or which carries a magnetic body 64 so as to attract and hold an insert ring 65 thereupon. The body surface 63 is formed with a tapered end 66 that is complementary to the shape of the insert ring 65, as will be described later by reference to FIG. 7. Because the pressing body 61 is engaged the electrode 52, electrical current will flow through the pressing body 61 and through the insert ring 65. As will become apparent later, when the insert ring 65 is engaged with the cylinder head 32, an electrical path will be formed through the cylinder head and base 45 to the conductor 55 to complete the electrical path. The insulated coating 59 on the mandrel 57 prevents short-circuiting around this area.

Figure 7:
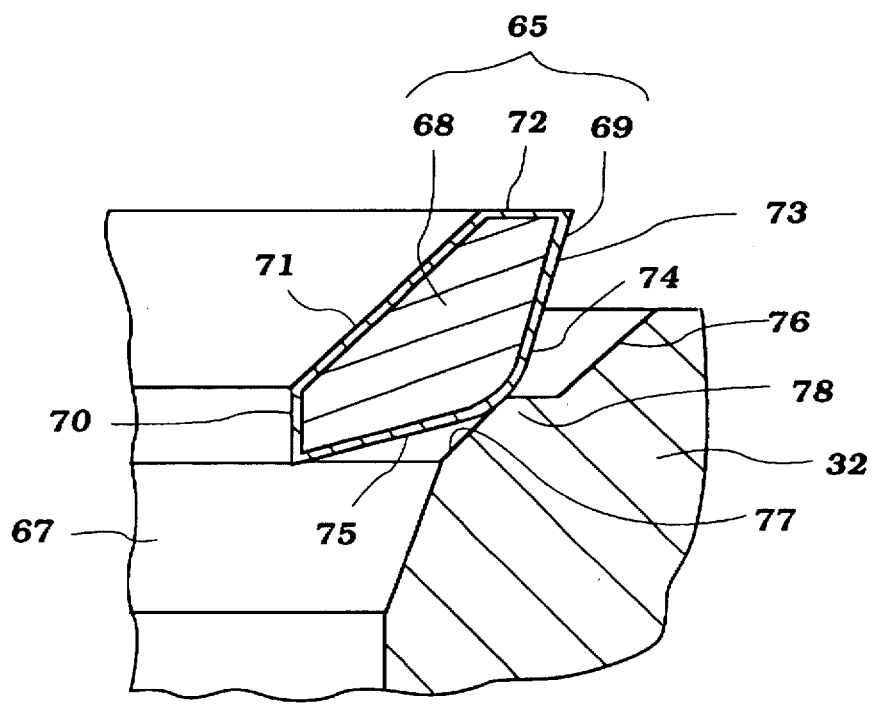
FIGS. 7–11 are step-by-step cross-sectional views showing the steps in pressing in and bonding a valve seat insert in accordance with the invention with FIG. 7 showing the initial step and FIG. 11 showing the final machined valve seat.

The construction of the insert ring 65, its shape and the shape of a cooperating recess 67 formed in the cylinder head at the mouth of the intake passage 34 will now be described by primary reference initially to FIG. 7. FIG. 7 is an enlarged cross-sectional view of one of the intake valve seats 35 and this description may be considered to be typical for that which may be utilized with the exhaust valves 41 to form the exhaust valve seats 39.

Basically, the valve seat 35 is formed by the insert ring, indicated by the reference numeral 65 and which has a metallurgical construction as will be described. This insert ring 65 is bonded to the cylinder head material 32 by a relatively thin metallurgical bonding layer that is formed in a manner which will be described. Adjacent this bonding layer, there is formed a portion of the material of the cylinder head 32 which has been plastically deformed. It should be noted that the alloy of the cylinder head 32 is of the same chemical composition and same physical structure, except for being slightly work hardened in the area adjacent the bonding layer, as in the remainder of the cylinder head material 32.

The insert ring 65, is formed from a Sintered ferrous alloy base 68 having a coating material filled within its intercices and also on its external surface as desired, which coating is indicated at 69. This material is preferably formed from a good electrical conductor such as copper. Copper also has another useful function as a coating for a reason to be described.

The insert ring 65 in accordance with this embodiment is formed with a cylindrical inner surface 70 that is relatively short in axial length and which merges into a tapered conical surface 71 which extends for a substantially length. The surface 71, which is actually the pressing surface, as will be described, ends in an end surface 72.

A first, conical outer surface section 73 extends at an acute angle to the axis of the cylindrical section 69 and merges at a rounded section 74 into an inclined lower end surface 75 which is formed at a greater angle than that of the conical surface 73. However, this angle is still an acute angle to a plane perpendicular to the axis of the cylindrical section 69.

The cylinder head material 32 is formed with a recess that is comprised of a first section 76 that is connected to a second section 77 that are joined by a horizontal surface that forms a projecting ledge 78 that contacts the rounded portion 74 of the insert ring 64 upon initial installation (FIG. 7). This tends to form a localized area that will begin the plastic deformation phase.

It has been noted that the copper coating serves the function of improving the electrical conductivity of the insert ring 65. Also, it has been noted that the copper performs additional functions. As should be apparent from the foregoing description, it is important that the bonding process not result in any alloying of the insert ring material and specifically that of the base 68 with the base material of the cylinder head 32.

The copper also serves the function of forming a eutectic alloy with the material of the cylinder head 32 which eutectic alloy has a lower melting point than either the melting point of the copper or that of the cylinder head material. As a result, the plastic deformation is accomplished with added ease and the metal can flow out during the pressing process as will be noted without large heat generation. In addition, the copper will react with any aluminum oxides that may be present on the surface of the recess 67 of the cylinder head 32 so as to extrude these oxides and provide a purer finish.

Preferably, the copper plating is done by electroplating and has a thickness in the range of 0.1–30 µm. Also, the cylinder head material of the body 32 is preferably an aluminum alloy as set forth in Japanese Industrial Standard (JIS) AC4C.

Figure 6:
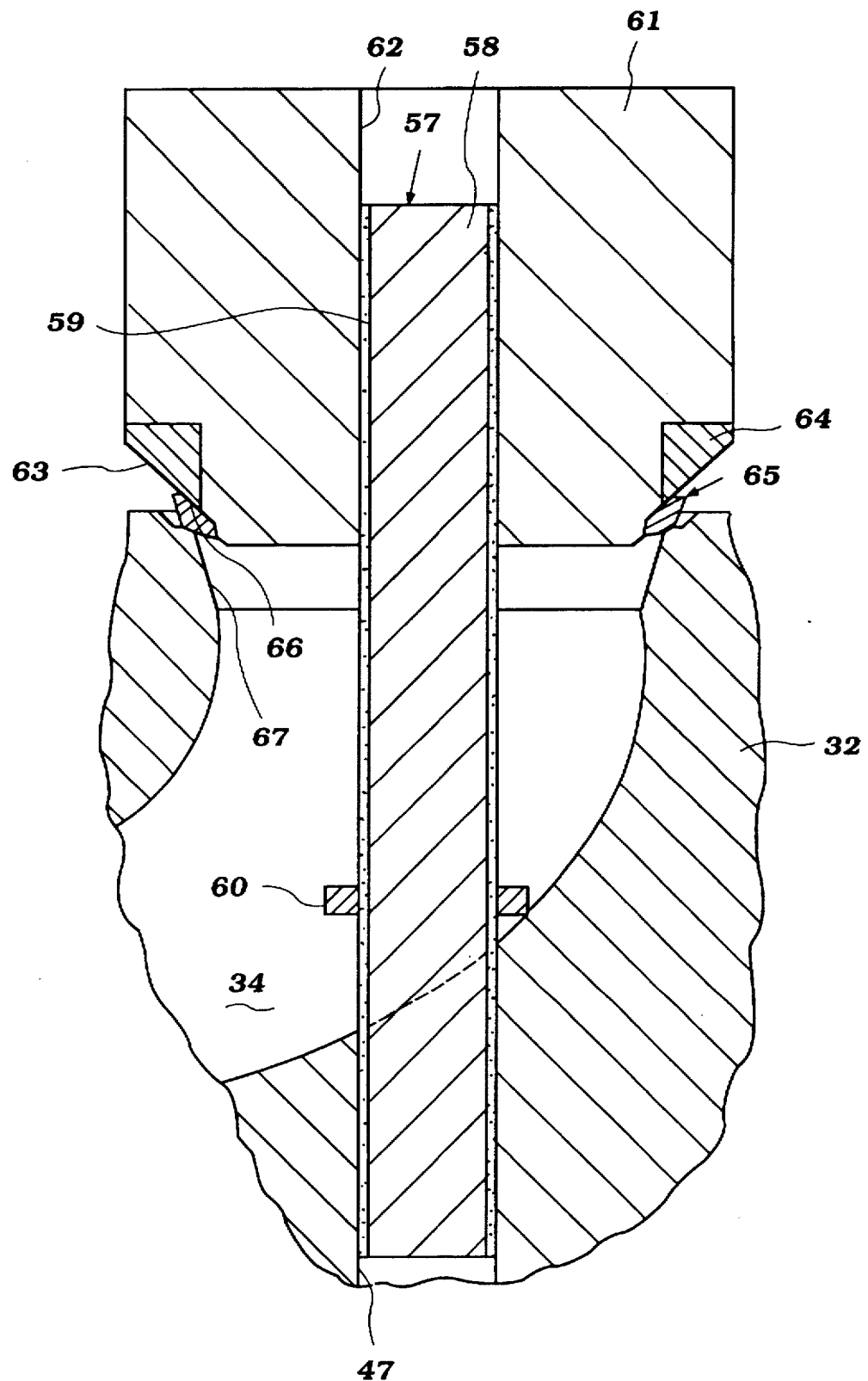
FIG. 6 is an enlarged cross-sectional view showing the apparatus in position for forming the bonded valve seat.

Beginning now to describe the pressing operation by reference to FIGS. 7–11, FIG. 7 shows the conditions comparable to that in FIG. 6. The pressing force is then applied by actuating the hydraulic ram operating motor 51 so as to move the electrode 52 into contact with the pressing mandrel electrode 59. Prior to this the mandrel 59 may be rotated to ensure that the insert ring 65 is correctly seated.

Figure 12:
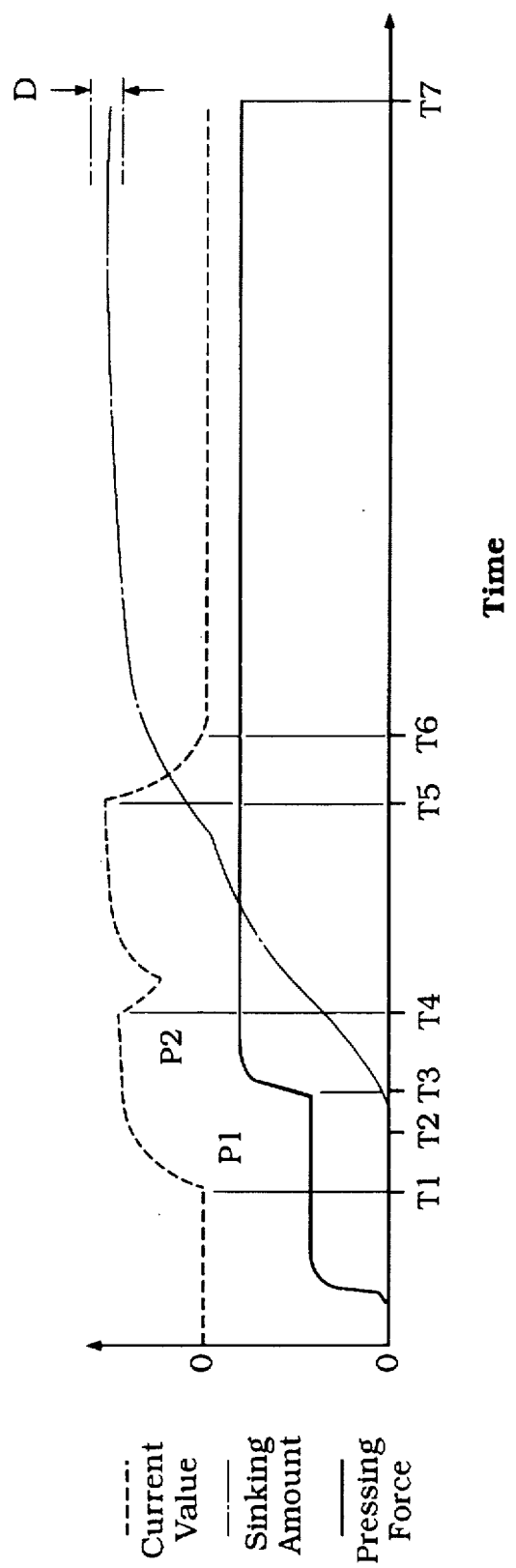
FIG. 12 is a graphical view showing pressing force and electric current flow in accordance with a preferred method of practicing the invention to achieve a bonded valve seat.

A pressing force is then applied at a force indicated at the force PI in FIG. 12. This force acts along the center axis of the seat and is maintained up until the time T1 wherein an electric current flow through the joint is initiated. When this occurs, there will be a high electrical resistance due to the small contact area and a plastic deformation begins in the range indicated at A in FIG. 8 so as to displace the material of the cylinder head 32.

Figure 8:
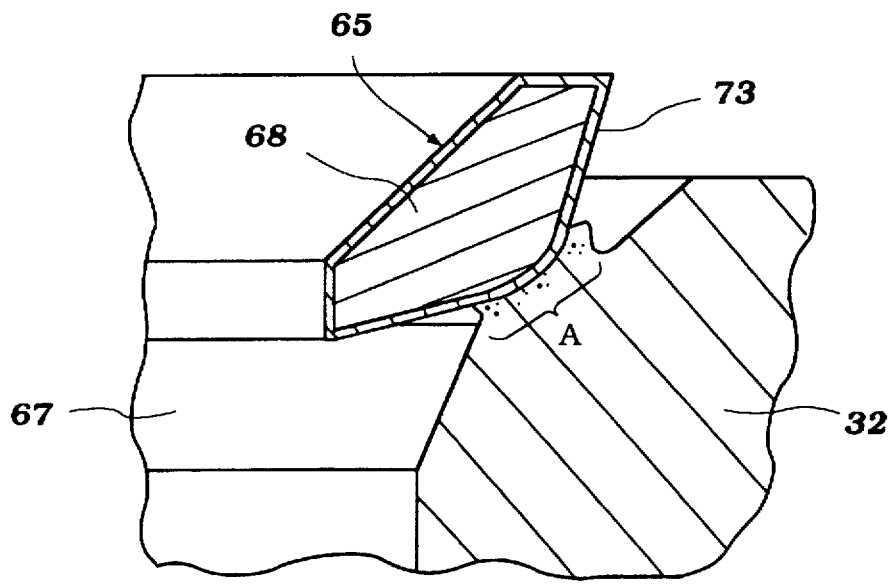

As the current is built up, the material will reach a temperature wherein the internal resistance is high enough to cause the copper coating layer 69 to defuse into the cylinder head material in the area 78 or shown in the range A so as to form the eutectic alloy that results in the area indicated at A in FIG. 8 and which eventually causes displacement and a plastic deformation and the insert ring 65 will begin to become embedded in the material of the cylinder head 32.

Figure 9:
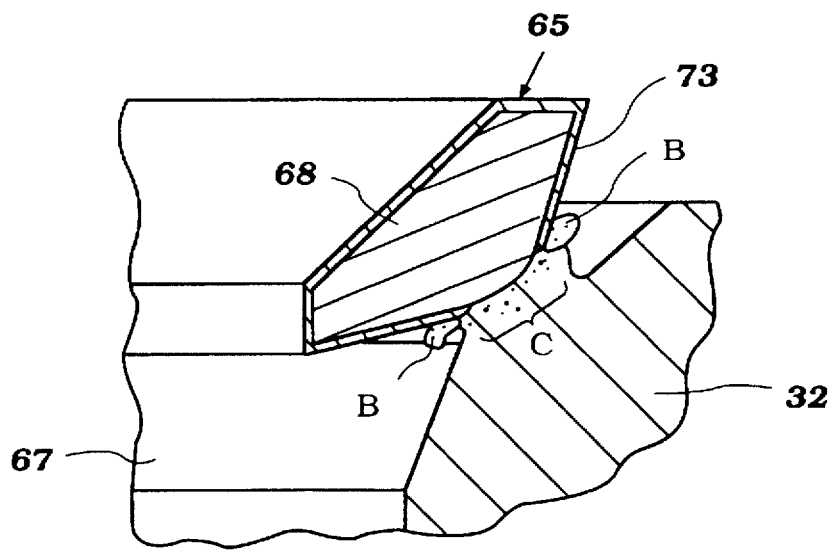

The eutectic layer is displaced as indicated at B in FIG. 9 toward the area which will be removed from where the final valve seat will be formed. Said another way, this material will be later machined away.

The actual deformation of the insert into the cylinder head body, as measured by the sensor 54, begins at the point in time T2. At some time thereafter, the electric current will have reached its maximum amount at the first level at the point T3 and then the pressing pressure is increased from the pressure P1 to a new higher pressure P2 which is then held.

This plastic deformation then continues and after a certain deflection and at the time period T4, the electric current is reduced sharply toward zero as shown in FIG. 12. This is done to avoid overheating and to ensure that there will be no alloying of the insert ring material and that of the cylinder head material. There will, however be atomic diffusion of the materials in the area C.

Figure 10:
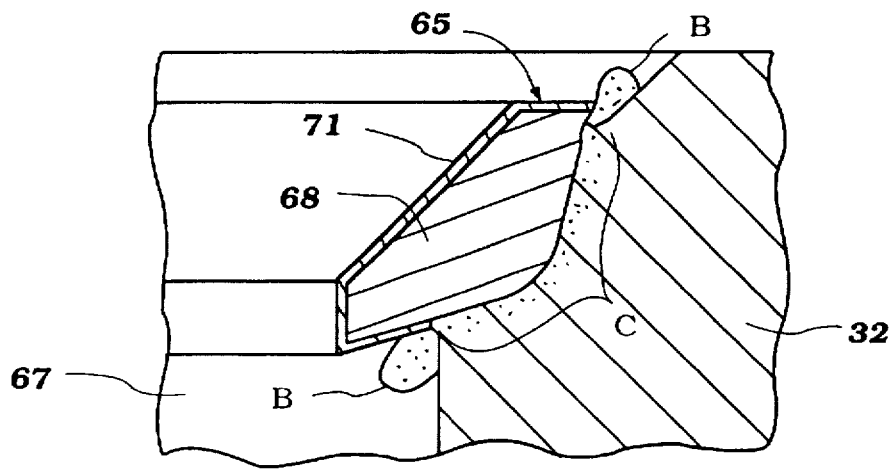

The electric current is then built up higher to a new level equal to or slightly higher than that before and is held at this level until the point in time T5. This pressing is continued after this still at the pressure P2 during which time period the current flow is dropped back to zero at the time period T6 while pressing is continued. The final joint appears as shown in FIG. 10 and it will be seen that substantially all of the eutectic alloy has been pushed from the area between the insert base 68 and the base cylinder head material resulting in only the work hardened adjacent the joint and atomic bonding in the area C. In addition, the metallurgical bonding will be completed.

During this time and after the completed bonding, the apparatus measures the amount of actual embedding of the insert ring 65 into the cylinder head 32. There is an allowable range as indicated by the dimension D in FIG. 12 which range is about 0.5 millimeters to 2 millimeters and preferably in the range of 1 to 1½ millimeters. In accordance with a feature of the invention if the sinking level is not reached in this range, then it can be assumed that the joint is not satisfactory. This judgment may also be made during the actual pressing, bonding operation. If the deflection is not in the proper range, the process may be discontinued.

In addition and in accordance with another feature of the invention, ajudgment may be made whether the main current values and total energization time are in the allowable range. If this is also met, then certain cylinder head valve seats may be actually pull testing to assure accuracy and satisfaction of the entire lot of cylinder head formed.

The way this testing is done is that a tensile force is applied by putting an appropriate fixture under the projecting edge of the insert ring as shown in FIG. 10 and applying a pulling force. An actual apparatus for performing this test is illustrated and will be described in conjunction with FIG. 13.

Figure 13:
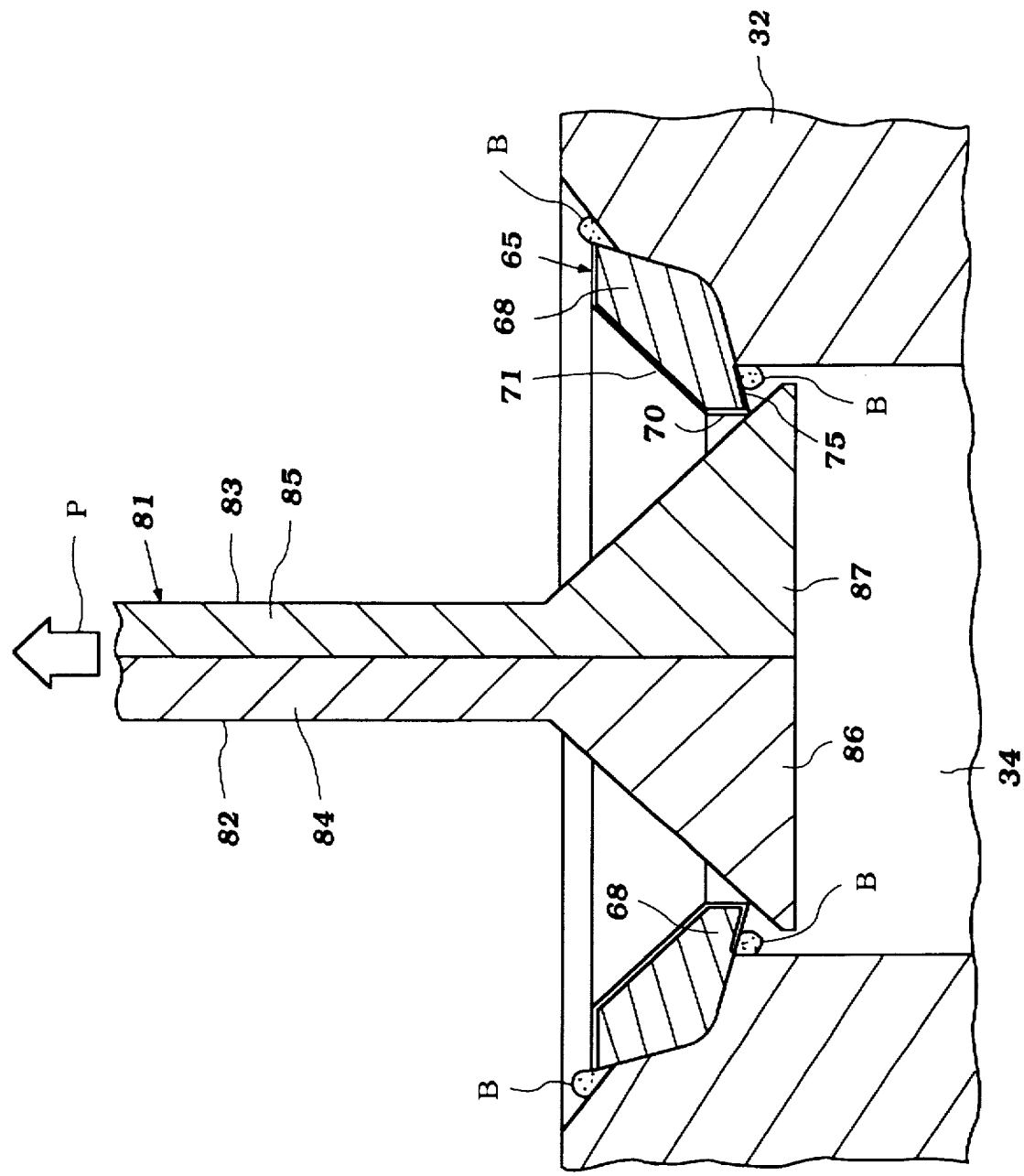
FIG. 13 is an enlarged cross-sectional view, in part similar to FIG. 10 and shows the test procedure for testing the strength of the resulting bonded joint.

As may be seen in FIG. 13, there is provided a jig or fixture, indicated generally by the reference numeral 81 and which has a configuration which generally corresponds to a poppet valve. However, this fixture is split through the middle into two halves 82 and 83, each of which has a shank portion 84 and 85, and a headed portion 86 and 87. This jig or fixture 81 is first inserted into the opening of the insert ring by shifting the halves 82 and 83 axially relative to each so that the effective diameter will be less than the diameter of the cylindrical inner surface 70. Once both halves 82 and 83 are in place, then the halves are shifted to the condition shown in FIG. 13 and the combined jig and fixture 81 is locked in position and is elevated. This elevation continues until the inclined surface of the headed portions 86 and 87 contact the under surfaces of the insert ring 65. As has been noted, the inner diameter of the cylindrical inner surface 70 is less than the diameter of the cylinder head flow passage so that this can be done.

A force is then exerted in the direction of the arrow P while the cylinder head 32 is held and this force is continued until the insert ring 65 is pulled free of the cylinder head 32. This way, the actual force necessary to separate the bonded joint can be measured. If the samples are within the predetermined range, then it can be assumed that all heads in the lot, which have also passed the other test, are satisfactory.

In addition to these tests, in accordance with further features of the invention there can be a heat endurance test and/or heat shock test applied to the finished cylinder head. All of these things are done before the final machining.

The heat endurance test is performed on the cylinder head in the state shown in FIG. 10. The head is kept in a furnace at 300° C. and atmospheric pressure in the range of 24 to 200 hours. A further pulling test is then performed using an apparatus as shown in FIG. 13 and the area inspected for separation or cracks.

In a heat shock test, the finished cylinder head in the condition shown in FIG. 10 is heated to 300° C. in a furnace at that temperature and atmospheric conditions. The thus heated head is then immediately immersed in ice water at 0° C. This procedure is repeated ten times and then the cylinder head is checked for separation force using an apparatus as seen in FIG. 13 and cracks and the separation test aforenoted is performed.

Figure 11:
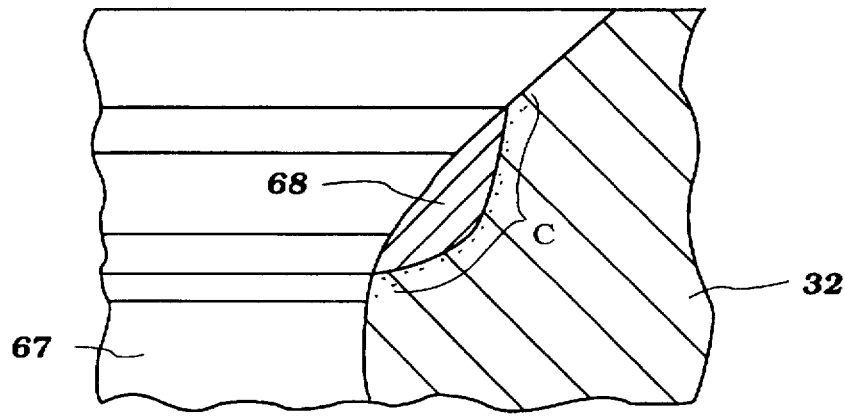

Assuming that the tests indicate that the head lot is satisfactory, then the heads are finish machined by grinding or the like to the conditions shown in FIG. 11. Thus, it will be seen that all of the eutectic alloy phase B is removed and only the metallurgical bonding area C remains. The finished joint has no melt reaction layer or no actual alloying between the cylinder head material and that of the insert ring.

A visual inspection is also made in accordance with another feature of the invention after the bonding is completed and before any machining. In this inspection it is checked to see that the eutectic alloy portion B (FIG. 10) extends around the entire insert without voids. If not the piece should be rejected as the bond may have voids.

Figure 14:
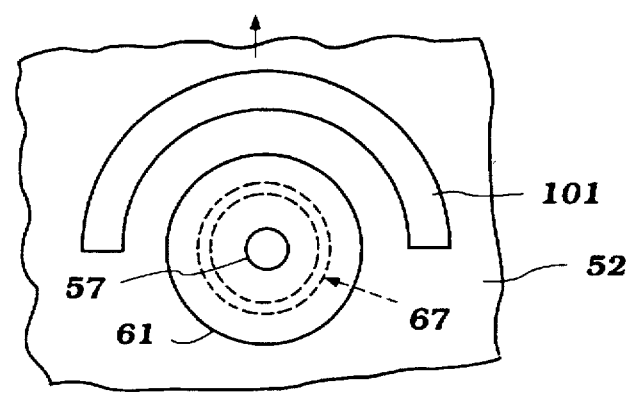
FIG. 14 is a top plan view showing a shield device that can be utilized with the pressing electrode to control the direction the eutectic alloy is removed from the bonded portion.

FIG. 14 shows another embodiment and in this embodiment the electrode 52 of the pressing head is provided with a ferrous semi-circular shield 101 which functions to provide a magnetic flux in the magnetic field which directs the eutectic alloy that is removed from the bonded area. This can be done so as to ensure that more of the eutectic alloy is disposed in the area where the most machining will occur so as to minimize the amount of machining necessary. Also this is done to insure complete bonding around the joint.

Figure 15:
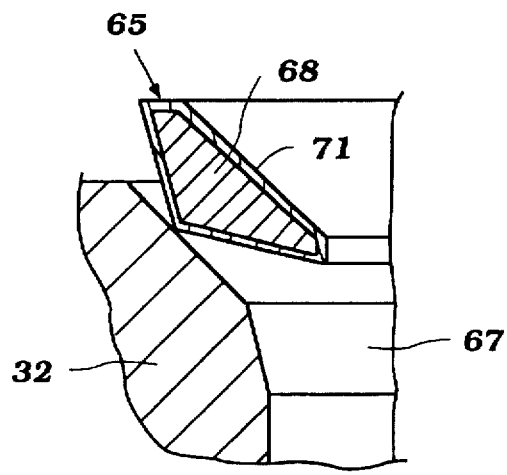
FIG. 15 is a cross-sectional view, in part similar to FIG. 7, and shows another configuration that may be employed for the insert and cylinder head.
Figure 16:
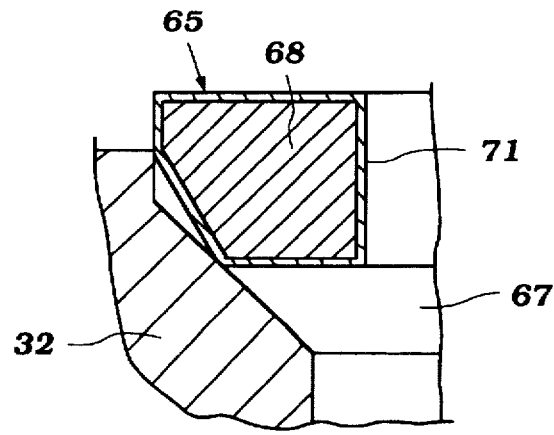
FIG. 16 is an enlarged cross-sectional view, in part similar to FIGS. 7 and 15, and shows yet another configuration which may be employed for the insert and the cylinder head recess.
Figure 17:
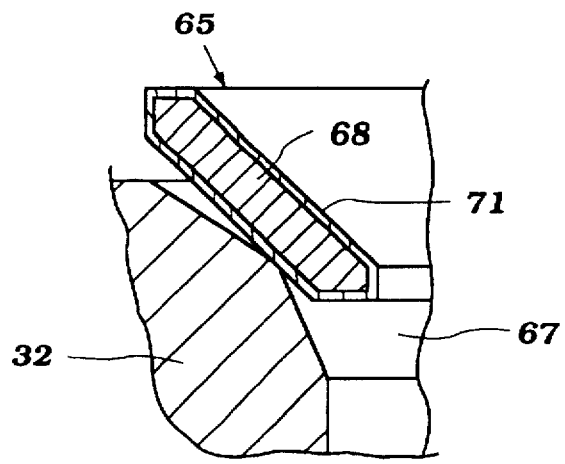
FIG. 17 is a cross-sectional view, in part similar to FIGS. 7, 15 and 16, and shows a still further configuration of insert that may be employed.

In the foregoing description, a specific shape of insert and cylinder head recess has been depicted and described. The insert and recess may take different configurations as shown in FIGS. 15-17. FIG. 15 shows a configuration similar to that of the previous embodiment, but the cylinder head recess is merely formed with a simple taper. In addition, the insert is not rounded, but the bonding operating will begin at a small area as in the previously described embodiment.

FIG. 16 shows another embodiment using a different shape ring and that lends itself to what is called end pressing. However, the shape of the insert ring is again such that the initial deformation of the cylinder head will begin at the middle of its tapered area. In addition, an outer peripheral groove will assist in locating.

FIG. 17 shows a simplified form of shape of insert ring that adapts itself to the pressing method which can be utilized with all of the embodiments of FIGS. 1-14. Again, however, the arrangement is designed so as to ensure localized initial deformation. Also, each of these embodiments are designed so as to provide the desired length of bonding surface to provide the desired bonding strength. Also, although a specific cylinder head material and insert material have been disclosed, various other materials may also be practiced.

Thus, from the foregoing description it should be readily apparent that the described pressing and bonding methods provide very effective valve seats that will eliminate sacrifices in strength and port configuration over conventional methods and methods whereby the validity of the bonds may be checked both during and after the bonding process. In addition, because of better heat transfer, lighter weight valves can be utilized and larger valve areas can be employed so as to increase the performance of the engine without shortening its life. Of course, the foregoing description is that of the preferred embodiment of the invention, and various changes and modifications may be made without departing from the spirit and scope of the invention, as defined by the appended claims.

What is claimed:

1. A method of affixing and testing a valve seat insert in a cylinder head having a flow passage ending in a combustion chamber recess, said method comprising the steps of forming a recess in said cylinder head at the base of the flow passage, forming an insert to be received in said recess and having an opening adapted to form a flow opening registering with said cylinder head flow passage and an outer surface positioned to engage the part of said cylinder head defining said recess, placing said insert in alignment with said recess, applying pressure to said cylinder head and said insert for forcing said insert into said recess, passing an electrical current through said pressing member, said insert and said cylinder head during at least a portion of said pressing operation to heat said cylinder head and metallurgically bond said insert and said cylinder head, monitoring the amount of depression of said insert into said recess in respect to time, and comparing the amount of depression with a known range of values to assure that the bonding of said insert to said cylinder head is satisfactory.

2. A method of affixing and testing a valve seat insert into a cylinder head of claim 1, wherein the electrical current is applied at a first amount for a first time and then is decreased and subsequently increased for a second time.

3. A method of affixing and testing a valve seat insert into a cylinder head of claim 2, wherein the pressure applied is held at a first value until a predetermined time before the electrical current flow is increased the second time.

4. A method of affixing and testing a valve seat insert into a cylinder head of claim 3, wherein the pressure is increased to a second higher value before the electrical current flow is increased the second time.

5. A method of affixing and testing a valve seat insert into a cylinder head of claim 4, wherein the current amount is also compared with known values for the resulting depressions.

6. A method of affixing and testing a valve seat insert into a cylinder head of claim 5, wherein the pressure is held at the second value until the bonding is completed.

7. A method of affixing and testing a valve seat insert into a cylinder head of claim 6, wherein the pressure is applied before the electric current flow is started.

8. A method of affixing and testing a valve seat insert in a cylinder head as set forth in claim 1, wherein the insert is sized to form an inwardly projecting shoulder around the recess at the end of the bonding step and further applying a pulling force to said shoulder while restraining said cylinder head to measure the force required to separate the bonded insert from the cylinder head.

9. A method of affixing and testing a valve seat insert in a cylinder head as set forth in claim 8, wherein the pulling force is applied by a split jig adapted to be inserted into the insert recess in engagement with the underside of the shoulder for applying the pulling force.

10. A method of affixing and testing a valve seat insert in a cylinder head as set forth in claim 9, wherein the jig has a configuration of a poppet-type valve.

11. A method of affixing and testing a valve seat insert in a cylinder head as set forth in claim 8, further including the step of heating the cylinder head and bonded insert to a temperature of about 300° C. for a period of about 24 hours and then cooling the cylinder head to room temperature before applying the pulling force.

12. A method of affixing and testing a valve seat insert in a cylinder head as set forth in claim 11, wherein the immediately bonded joint is first subjected to a pulling test before the heating and cooling and a subsequent pulling test is performed in the same manner.

13. A method of affixing and testing a valve seat insert in a cylinder head as set forth in claim 8, wherein the cylinder head and bonded valve seat are heated to an elevated temperature and immediately quenched to the temperature of freezing water for a number of cycles before applying the pulling test.

14. A method of affixing and testing a valve seat insert in a cylinder head as set forth in claim 13, wherein the heating and cooling and pulling tests are applied after the prior successful performance of a pulling test at the completion of the bonding cycle.

15. A method of affixing and testing a valve seat insert in a cylinder head as set forth in claim 8, further including the step of placing a coating on at least the portion of the insert that will contact the portion of the cylinder head that forms the recess, the amount of electrical current flow through said insert and said cylinder head being sufficient to melt said coating and form an eutectic alloy with the cylinder head material, the pressure being applied until the eutectic alloy is substantially extruded from the area between the insert and the cylinder head and metallurgically bond the insert and cylinder head, and visually inspecting the resulting bond to insure that eutectic alloy has been extruded around the entire resulting joint.

16. A method of affixing and testing a valve seat insert in a cylinder head as set forth in claim 15, wherein the pulling force is applied by a split jig adapted to be inserted into the insert recess in engagement with the underside of the shoulder for applying the pulling force.

17. A method of affixing and testing a valve seat insert in a cylinder head as set forth in claim 16, wherein the jig has a configuration of a poppet-type valve.

18. A method of affixing and testing a valve seat insert in a cylinder head as set forth in claim 16, further including the step of heating the cylinder head and bonded insert to a temperature of about 300° C. for a period of about 24 hours and then cooling the cylinder head to room temperature before applying the pulling force.

19. A method of affixing and testing a valve seat insert in a cylinder head as set forth in claim 18, wherein the immediately bonded joint is first subjected to a pulling test before the heating and cooling and a subsequent pulling test is performed in the same manner.

20. A method of affixing and testing a valve seat insert in a cylinder head as set forth in claim 15, wherein the cylinder head and bonded valve seat are heated to an elevated temperature and immediately quenched to the temperature of water freezing for a number of cycles before applying the pulling test.

21. A method of affixing and testing a valve seat insert in a cylinder head as set forth in claim 20, wherein the heating and cooling and pulling test is applied after the successful performance of a pulling test at the completion of the bonding cycle.

22. A method of affixing and testing a valve seat insert in a cylinder head having a flow passage ending in a combustion chamber recess, said method comprising the steps of forming a recess in said cylinder head at the base of the flow passage, forming an insert to be received in said recess and having an opening adapted to form a flow opening registering with said cylinder head flow passage and an outer surface positioned to engage the part of said cylinder head defining said recess, placing said insert in alignment with said recess, applying pressure to said cylinder head and said insert for forcing said insert into said recess, passing an electrical current through said pressing member, said insert and said cylinder head during at least a portion of said pressing operation to heat said cylinder head and metallurgically bond said insert and said cylinder head, said insert being sized to form an inwardly projecting shoulder around said recess at the end of the bonding step, and applying a pulling force to said shoulder while restraining said cylinder head to measure the force required to separate the bonded insert from the cylinder head.

23. A method of affixing and testing a valve seat insert in a cylinder head as set forth in claim 22, wherein the pulling force is applied by a split jig adapted to be inserted into the insert recess in engagement with the underside of the shoulder for applying the pulling force.

24. A method of affixing and testing a valve seat insert in a cylinder head as set forth in claim 23, wherein the jig has a configuration of a poppet-type valve.

25. A method of affixing and testing a valve seat insert in a cylinder head as set forth in claim 23, further including the step of heating the cylinder head and bonded insert to a temperature of about 300° C. for a period of about 24 hours and then cooling the cylinder head to room temperature before applying the pulling force.

26. A method of affixing and testing a valve seat insert in a cylinder head as set forth in claim 25, wherein the immediately bonded joint is first subjected to a pulling test before the heating and cooling and a subsequent pulling test is performed in the same manner.

27. A method of affixing and testing a valve seat insert in a cylinder head as set forth in claim 23, wherein the cylinder head and bonded valve seat are heated to an elevated temperature and immediately quenched to the temperature of water freezing for a number of cycles before applying the pulling test.

28. A method of affixing and testing a valve seat insert in a cylinder head as set forth in claim 20, wherein the heating and cooling and pulling test is applied after the successful performance of a pulling test at the completion of the bonding cycle.

29. A method of affixing and testing a valve seat insert in a cylinder head having a flow passage ending in a combustion chamber recess, said method comprising the steps of forming a recess in said cylinder head at the base of the flow passage, forming an insert to be received in said recess and having an opening adapted to form a flow opening registering with said cylinder head flow passage and an outer surface positioned to engage the part of said cylinder head defining said recess, placing a coating on at least the portion of the insert that will contact the portion of the cylinder head that forms the recess, placing said insert in alignment with said recess, applying pressure to said cylinder head and said insert for forcing said insert into said recess, passing an electrical current through said pressing member, said insert and said cylinder head during at least a portion of said pressing operation to heat said cylinder head, the amount of electrical current flow through said insert and said cylinder head being sufficient to melt said coating and form an eutectic alloy with the cylinder head material, the pressure being applied until the eutectic alloy is substantially extruded from the area between the insert and the cylinder head and metallurgically bond the insert and cylinder head, and visually inspecting the resulting bond to insure that eutectic alloy has been extruded around the entire resulting joint.

* * * * *